US012379343B2

(12) United States Patent
Johnson, Jr. et al.

(10) Patent No.: US 12,379,343 B2
(45) Date of Patent: Aug. 5, 2025

(54) SCALABLE BACK-GATED FUNCTIONALIZED GRAPHENE FIELD EFFECT TRANSISTORS FOR DETECTION OF DNA AND OTHER TARGET MOLECULES

(71) Applicant: THE TRUSTEES OF THE UNIVERSITY OF PENNSYLVANIA, Philadelphia, PA (US)

(72) Inventors: Alan T. Johnson, Jr., Philadelphia, PA (US); Jinglei Ping, Gaithersburg, MD (US); Ramya Vishnubhotla, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 300 days.

(21) Appl. No.: 17/934,540

(22) Filed: Sep. 22, 2022

(65) Prior Publication Data
US 2023/0055137 A1  Feb. 23, 2023

Related U.S. Application Data

(63) Continuation of application No. 16/084,739, filed as application No. PCT/US2017/022108 on Mar. 13, 2017, now abandoned.

(60) Provisional application No. 62/308,010, filed on Mar. 14, 2016.

(51) Int. Cl.
| G01N 27/327 | (2006.01) |
| B82Y 15/00 | (2011.01) |
| G01N 27/414 | (2006.01) |
| G01N 33/543 | (2006.01) |

(52) U.S. Cl.
CPC ............ *G01N 27/327* (2013.01); *B82Y 15/00* (2013.01); *G01N 27/4146* (2013.01); *G01N 33/5438* (2013.01)

(58) Field of Classification Search
CPC ............ G01N 27/327; G01N 27/4146; G01N 33/5438; B82Y 15/00
See application file for complete search history.

(56) References Cited

U.S. PATENT DOCUMENTS

| 3,808,195 A | 4/1974 | Shelso et al. |
| 10,809,222 B2 | 10/2020 | Johnson et al. |
| 2012/0220053 A1 | 8/2012 | Lee et al. |
| 2014/0332213 A1 | 11/2014 | Zhou et al. |
| 2014/0332214 A1 | 11/2014 | Zhou et al. |
| 2015/0096751 A1 | 4/2015 | Shen et al. |
| 2016/0264421 A1* | 9/2016 | Lobez Comeras ......... C23C 16/0272 |

FOREIGN PATENT DOCUMENTS

| WO | 2014/145377 A1 | 9/2014 |
| WO | 2014/176524 A2 | 10/2014 |
| WO | 2014/182169 A2 | 11/2014 |
| WO | 2016/112079 A1 | 7/2016 |

OTHER PUBLICATIONS

Ping et al, (post art) Scalable Production of High-Sensitivity, LabelFree DNA Biosensors Based on Back-Gated Graphene Field Effect Transistors. (Year: 2016).*
Dubuisson et al., "Optimizing Label-Free DNA Electrical Detection on Graphene Platform", Anal. Chem., 2011, vol. 83, No. 7, pp. 2452-2460, DOI: 10.1021/ac102431d.
Guangyu et al., "Electrophoretic and Field-Effect Graphene for All-Electrical DNA Array Technology", Nature Communications, 2014, vol. 5, Article No. 4866, pp. 1-9, DOI: 10.1038/ncomms5866.
Vieira et al., "Human Papillomavirus E6 Triggers Upregulation of the Antiviral and Cancer Genomic DNA Deaminase APOBEC3B", C. MBio, 2014, vol. 5, Issue 6, e02234-14, pp. 1-8, DOI:10.1128/mBio.02234-14.

* cited by examiner

*Primary Examiner* — Narayan K Bhat
(74) *Attorney, Agent, or Firm* — BakerHostetler (57) ABSTRACT

Provided are devices and methods for detecting a target molecule, based on using a graphene electrode. The devices exhibit high sensitivity to target molecules such as DNA that may be present at comparatively low concentrations.

12 Claims, 8 Drawing Sheets
Specification includes a Sequence Listing.

SEQUENCE LISTING

```
Sequence total quantity: 5
SEQ ID NO: 1              moltype = DNA  length = 22
FEATURE                   Location/Qualifiers
source                    1..22
                          mol_type = other DNA
                          organism = synthetic construct
SEQUENCE: 1
catgatgagt attagactta ct                                           22

SEQ ID NO: 2              moltype = DNA  length = 22
FEATURE                   Location/Qualifiers
source                    1..22
                          mol_type = other DNA
                          organism = synthetic construct
SEQUENCE: 2
caggtagttg catgttgttg gg                                           22

SEQ ID NO: 3              moltype = DNA  length = 22
FEATURE                   Location/Qualifiers
source                    1..22
                          mol_type = other DNA
                          organism = synthetic construct
SEQUENCE: 3
taggtagttg catgttgttg gg                                           22

SEQ ID NO: 4              moltype = DNA  length = 22
FEATURE                   Location/Qualifiers
source                    1..22
                          mol_type = other DNA
                          organism = synthetic construct
SEQUENCE: 4
caggtagttt catgttgttg gg                                           22

SEQ ID NO: 5              moltype = DNA  length = 22
FEATURE                   Location/Qualifiers
source                    1..22
                          mol_type = other DNA
```

```
                               -continued
                    organism = synthetic construct
SEQUENCE: 5
taggtagttt catgttgttg gg                                        22
```

SCALABLE BACK-GATED FUNCTIONALIZED GRAPHENE FIELD EFFECT TRANSISTORS FOR DETECTION OF DNA AND OTHER TARGET MOLECULES

RELATED APPLICATIONS

The present application is a continuation of U.S. patent application Ser. No. 16/084,739, "Scalable Back-Gated Functionalized Graphene Field Effect Transistors For Detection Of DNA And Other Target Molecules" (filed Sep. 13, 2018): which application is a national stage application of International Patent Application No. PCT/US2017/022108, "Scalable Back-Gated Functionalized Graphene Field Effect Transistors For Detection Of DNA And Other Target Molecules" (filed Mar. 13, 2017); which application claims priority to and the benefit of U.S. Patent Application No. 62/308,010, "Scalable Back-Gated Functionalized Graphene Field Effect Transistors For Detection Of DNA And Other Target Molecules" (filed Mar. 14, 2016), the entireties of which foregoing applications are incorporated herein by reference for any and all purposes.

GOVERNMENT RIGHTS

This invention was made with government support under AI045008 awarded by the National Institutes of Health and W911NF-10-1-0093 awarded by the United States Army. The government has certain rights in the invention.

SEQUENCE LISTING XML

The instant application contains a Sequence Listing XML which is being submitted herewith electronically in XML format and is hereby incorporated by reference in its entirety. Said XML copy, created on Feb. 4, 2025, is named 16-7816_Sequence_Listing.xml and is 5,550 bytes in size.

TECHNICAL FIELD

The present disclosure relates to the field of molecular measurement and to the field of graphene devices.

BACKGROUND

With advancements in medical treatment and diagnostics has come a need for detection devices having high sensitivity to target molecules, such as ssDNA and other biomolecules. There is also a need for a platform sensor technology having a flexible design that can be adapted to detection of a variety of target molecules.

SUMMARY

In meeting the described needs, the present disclosure provides, inter alia, a sensitive sensor platform for drug detection. In some embodiments, the device's monitoring of a voltage signal allows for detection of complementary DNA at, e.g., a concentration of 100 pM, which is a factor of 10,000 improvement over existing alternatives. In some embodiments, the disclosure provides a graphene FET design functionalized with DNA oligomers that can detect cDNA and small molecule drug targets.

Graphene is a promising material for sensor applications due to its outstanding electrical and thermal properties, high tensile strength, and biocompatibility. Provided here are, inter alia, highly-scalable, back-gated arrays of single-strand DNA (ssDNA) decorated field-effect transistors (FETs), based on chemical-vapor-deposited graphene, for detection of complementary DNA.

In illustrative experiments, arrays having up to 100 graphene FETs were created with a scalable photolithography process with a layout suitable for multiplexed detection of up to four molecular targets. It should be understood that the present disclosure is not limited to arrayed devices having up to 100 graphene portions/FETs: a figure of 100 is illustrative only and it should be understood that the present disclosure provides devices that have a one or more graphene portions/FETs.

The presence of the DNA was confirmed with atomic force microscopy (AFM). Binding of molecular targets by the DNA chemical recognition element led to a reproducible, concentration-dependent shift in the Dirac voltage on the current-gate voltage characteristic, with a limit of detection less than 100 pM. Control experiments showed that the method is highly specific for the complementary ssDNA oligomer, discriminating fully against random ssDNA and by a factor of 104 against ssDNA with a single base mismatch. This biosensor class is useful in detection of amplicons in a system for quantitative DNA sequencing as well as detection of drugs or other targets for which a ssDNA aptamer is available.

In one aspect, the present disclosure provides sensor devices, comprising: a portion of graphene; and a polyaromatic molecule attached to and in electrical communication with the portion of graphene, the polyaromatic molecule comprising a leaving group configured to be displaced by an amine group.

In another aspect, the present disclosure provides sensor devices, comprising: a portion of graphene: a polyaromatic molecule attached to and in electrical communication with the portion of graphene, the polyaromatic molecule being in electronic communication with a detection moiety configured to interact with a target molecule.

Further provided are methods, comprising: contacting a sensor device according to the present disclosure with a sample; and measuring an electrical signal of the device related to an interaction between the detection moiety and the sample.

Additionally disclosed are methods, comprising: contacting a sample to a detection moiety attached to a portion of graphene, the detection moiety being attached to a polyaromatic molecule in electrical communication with a portion of graphene; and measuring an electrical signal of the device related to an interaction between the detection moiety and the sample.

Further provided are methods of fabricating a detector device, comprising: attaching a polyaromatic molecule to a portion of graphene so as to place the polyaromatic molecule into electrical communication with the portion of graphene: attaching a detection moiety to the polyaromatic molecule; and placing the portion of graphene into electrical communication with at least one electrode.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it can be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Because graphene is highly sensitive to small electrical changes, it is an ideal material for sensing applications. Biosensors based on graphene for DNA detection have broad applications. For instance, the binding and electrical signal of some biomolecule to a DNA strand can aid in the detection of drugs or chemicals in urine or blood:certain types of cancer may be detected through a graphene/DNA device due to the upregulation of a specific DNA strand from the presence of a malignant tumor.

The disclosed devices are scalable, back-gated DNA biosensors based on graphene, making them practical for commercial use. Multiple (e.g., 50 to 100) may be created at a time, and a chip-type design allows for the testing of multiple concentrations and/or multiple targets (e.g., DNA types) at once. The large-area, continuous graphene sheets grown by CVD and the well optimized photolithography procedure enables a yield of, e.g., over 90%.

EXEMPLARY EMBODIMENTS

Figure 1:
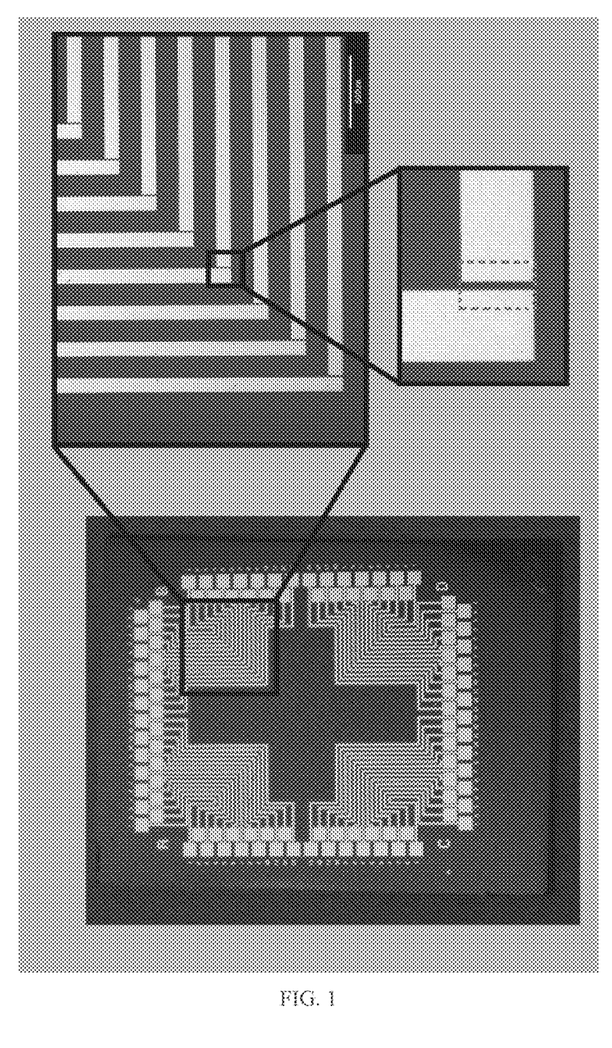
FIG. 1 provides (left) an optical micrograph of an exemplary chip with a GFET array and (right) higher magnification images with the channel of an exemplary, individual GFET shown by the dashed rectangle.

Field effect transistor (FET) devices were fabricated by photolithography from chemical vapor deposition (CVD) grown graphene, resulting in an array of devices with each graphene device having channel dimensions of 10 um by 100 um. FET devices were then functionalized with pyrene-N-hydroxysuccinimide (pyrene-NHS), which binds to the surface of the graphene via pi-pi stacking. The purpose of the pyrene-NHS molecule is to allow a strand of ssDNA with an amine group at the 5' end (referred to as the "probe" DNA) to bind to the pyrene group so that the DNA is immobilized on the graphene surface (FIG. 1).

Figure 2:
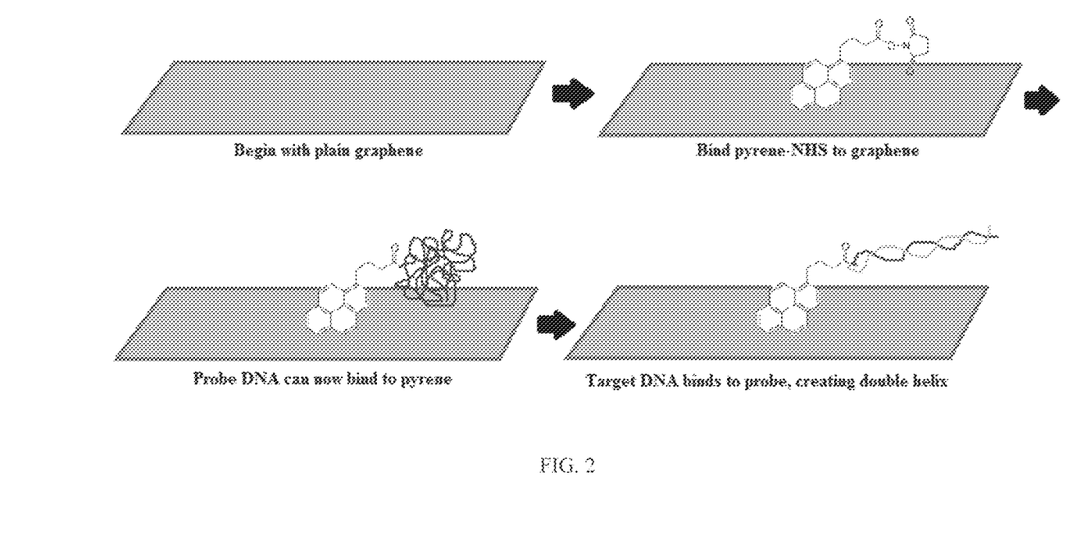
FIG. 2 provides an exemplary schematic of an attachment chemistry and detection experiment. Pyrene-NHS binds to the graphene via pi-pi (orbital) stacking, and the amine group of the probe DNA displaces the ester group of the pyrene-NHS molecule to bind the probe DNA. Target (or control) DNA attachment follows: the FIG. represents exposure to the target, which would hybridize with the probe.

AFM measurements were used to confirm binding of pyrene-NHS functionalization on the graphene surface and then again to confirm binding of probe DNA (FIG. 2). Once the probe attachment was completed, the devices were exposed to aqueous solutions containing various known concentrations of a complementary DNA strand, known as the "target" DNA. I-Vg curves for the devices were recorded both after probe attachment and again after exposure to the target.

It was found that exposure to the target solution led to a concentration-dependent shift in the Dirac voltage, with a detection limit of 100 pM. Control experiments were conducted to show that the method is specific for the complementary ssDNA oligomer. First, random (non-complementary) ssDNA at a concentration of 1 µM generated a response approximately equal to that of pure water. Second, ssDNA with a single base mismatch at 1 uM generated a response approximately equal to that of matched ssDNA at a concentration of 100 pM, demonstrating a selectivity against the single-base mismatch of $10^4$.

CVD graphene was grown using standard methods in a 4 inch furnace on a copper foil substrate with a methane source for carbon. 80 sccm of hydrogen gas was flowing through the furnace at all times, and the furnace reached 1020 deg. C and stayed at this temperature for one hour, to anneal the copper foil. After one hour, the methane source was introduced at 10 sccm, and growth lasted for 20 minutes at 1020 deg. C. Once the growth step was completed, the furnace was cooled to below: 100 C and the foil was removed for transfer.

The graphene foil transferred to an oxidized silicon wafer using the so-called "bubble transfer method." First, the graphene-copper growth substrate was coated with a sacrificial layer of polymethyl methacrylate (PMMA), and baked on a hot plate at 100 C for two minutes to ensure good adhesion between the graphene and PMMA. The PMMA/graphene film was then removed from the copper foil by an electrolysis process in a sodium hydroxide (NaOH) solution to help remove the PMMA/graphene film from the copper foil. This film was then transferred to a series of DI water baths for removing NaOH residue, and finally, scooped onto a patterned substrate with a previously fabricated array of electrodes. It should be understood that although electrodes may be pre-formed on a substrate, the electrodes may also be formed after graphene is disposed on the substrate.

The electrode substrate was created through the use of traditional photolithography steps on a commercially obtained silicon wafer with 300 nm of silicon dioxide. Chromium (5 nm) and gold (40 nm) contacts were defined using photolithography followed by thermal evaporation of the metals onto the wafer to prepare it for graphene transfer. Following graphene transfer, small channels between the electrodes were defined using photolithography, with dimensions of 10 um by 100 um.

Residual photoresist was removed and the devices were annealed in a 1 inch furnace at 225 C, with Ar flow of 1000 sccm and H2 flow of 250 sccm for one hour. FIG. 1 shows an optical micrograph of a GFET array and zoomed in micrographs showing an individual GFET device. The bulk of the silicon wafer is conducting and was used as the backgate electrode.

After the GFET array was cleaned and annealed, DNA attachment chemistry was performed, followed by the detection step. Devices were incubated in a solution of 2 mg of pyrenebutyric acid N-hydroxysuccinimide ester ("pyrene-NHS") in 25 mL of dimethyl formamide (DMF) for 20 hours. Following the pyrene-NHS attachment, devices were soaked in a 1 uM solution of probe DNA for 2 hours.

At this point, the devices were electrically characterized to provide a sensor baseline before the detection step. For the detection step, 1 mL of a known concentration of DNA (either a complementary target or a control oligomer) in deionized water was pipetted onto the device and then allowed to conjugate for 30 min in a humid environment. FIG. 2 is a schematic of the DNA attachment chemistry and detection step. The devices were electrically characterized once again to obtain the sensor response.

Figure 3:
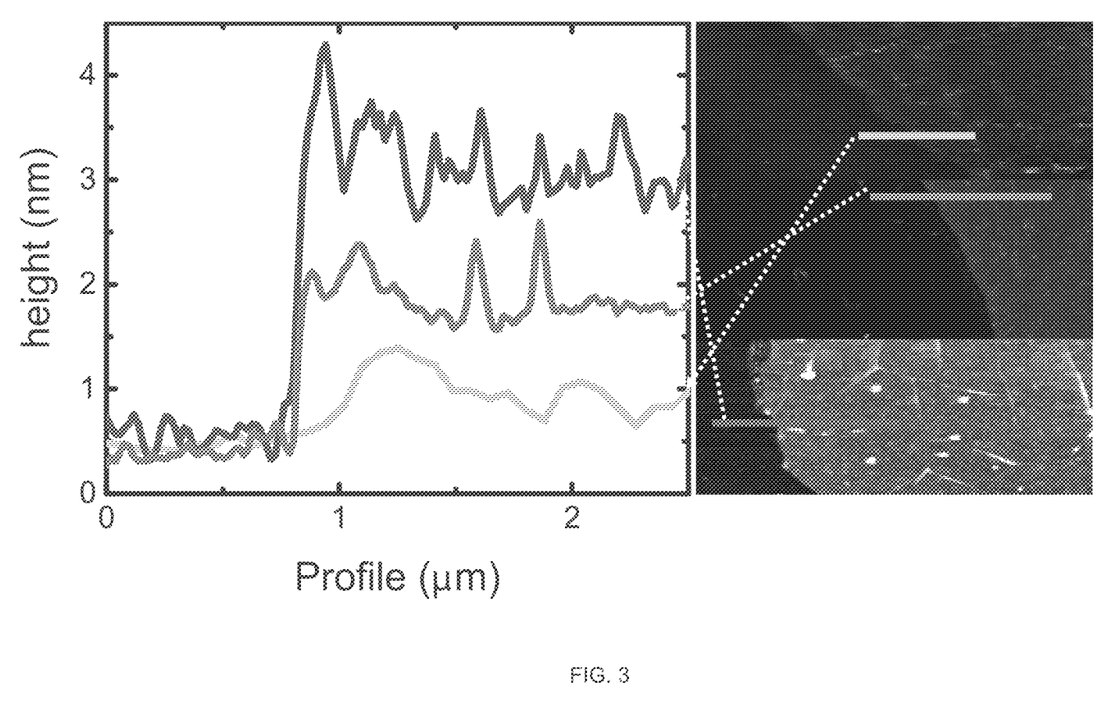
FIG. 3 provides exemplary line scans and corresponding AFM images for as-transferred graphene on $SiO_2$ substrate (light blue:lower trace at 1 um), graphene functionalized with pyrene-NHS (blue:middle trace at 1 um), and after ssDNA immobilization (dark blue:top trace at 1 um) (white arrows are used to identify particular data traces)

The AFM scans in FIG. 3 show that the attachment chemistry works in the desired manner. Bare graphene on the silicon wafer (light blue scan and top AFM image) has a height of about 1 nm. After PYR-NHS attachment, the height of the surface has increased to ~2 nm, showing uniform coverage. After exposure to probe DNA, the height is ~3.2 nm, consistent with the length of the DNA oligomer. The surface appears rough suggesting partial coverage of the surface with DNA exposed and available for hybridization.

Electrical Characterization

Figure 4:
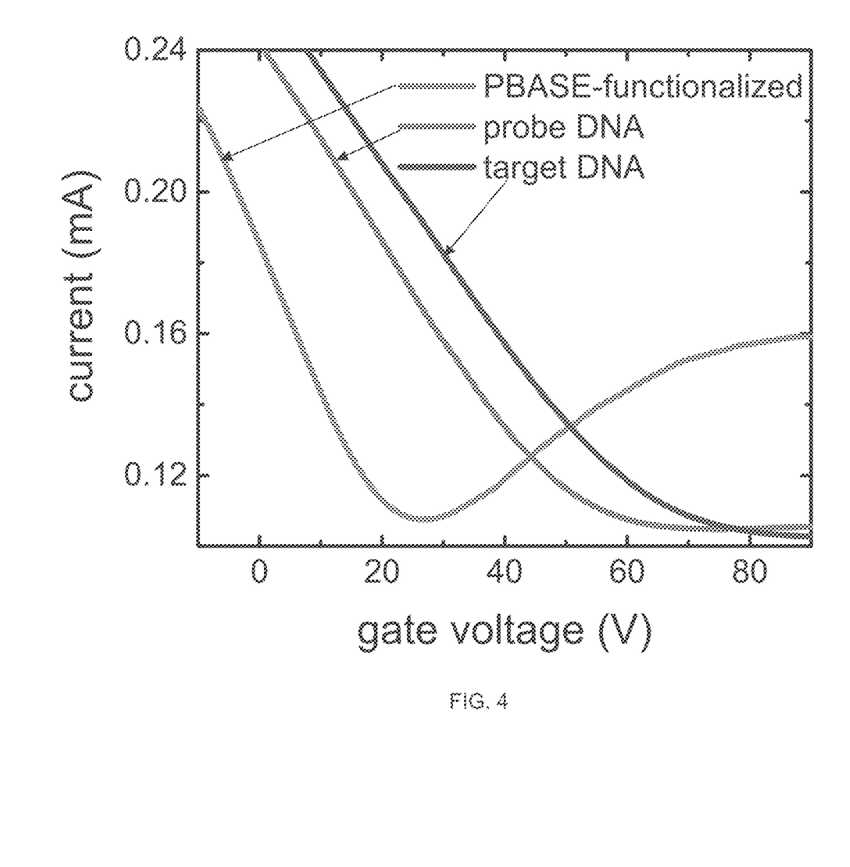
FIG. 4 provides exemplary current versus gate voltage curves for graphene devices after pyrene-NHS, probe DNA and target DNA attachment: each step is associated with a positive shift of the Dirac voltage (PBASE trace is bottom trace at 30 V, probe DNA is middle trace at 30 V, and target DNA is upper trace at 30 V)
Figure 5:
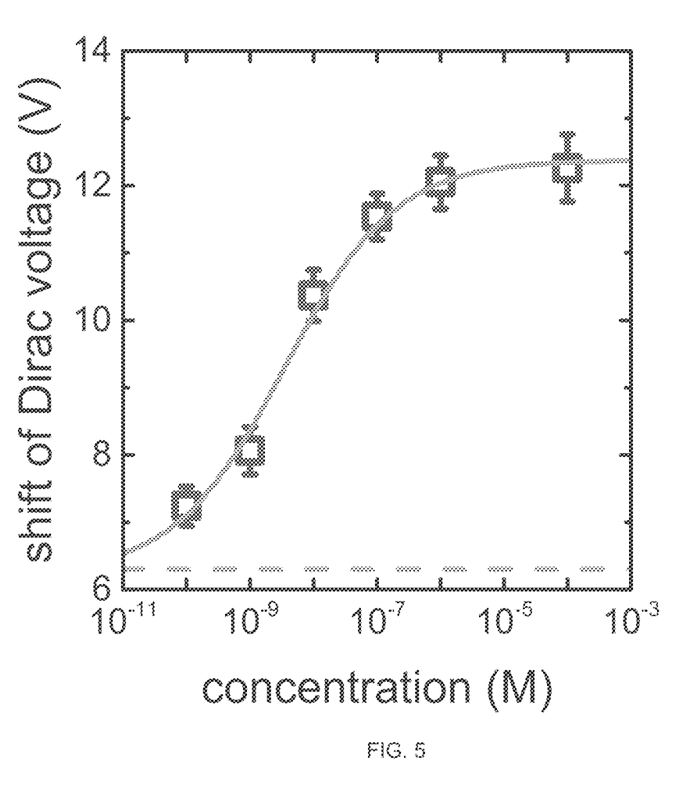
FIG. 5 provides an exemplary change in Dirac voltage versus concentration of DNA solution. The dashed blue line is the response to pure water. Each data point represents averaging of approximately 10 devices tested. The solid (blue) curve is a fit to a model based on the Hill-Langmuir equation.

Sensor response was determined using the current-back-gate voltage characteristic, specifically the Dirac voltage, the value of the back gate voltage corresponding to a conductance minimum (FIG. 4). There was a clear shift in the Dirac voltage due to pyrene-NHS and probe DNA attachment, and an additional Dirac voltage shift after exposure to target (FIG. 4). Furthermore, as concentration of the target DNA solution increased, so did the change in Dirac voltage (FIG. 5). Thus the Dirac voltage shift allows measurement of the concentration of complementary ssDNA. The lowest concentration of DNA tested was 100 pM (an exemplary level only: the disclosed technology is not limited in sensitivity to 100 pM), and this concentration was clearly differentiated from the response to pure DI water. A sensor may obtain a signal from a sample having a volume in the range of from about 0.1 to about 100,000 microliters and all intermediate values, e.g., from about 1 to about 10,000 microliters, from about 10 to about 5000 microliters, from about 100 to about 1000 microliters, or even about 500) microliters.

Control experiments were conducted to confirm that the sensor is specific for complementary ssDNA. First, the sensor response to pure water was measured as shown by the blue line in FIG. 5. The response to 100 pM of complementary ssDNA was clearly differentiated from the water response (>2 standard deviations). Second, the sensor response was measured to a 1uM solution of ssDNA that differed from the complementary DNA only in the identity of a single base. The response was about 7.0 V, comparable to the response to complementary DNA at a concentration of 100 pM, a factor of $10^4$ smaller.

Additional Biosensor Examples

Figure 6:
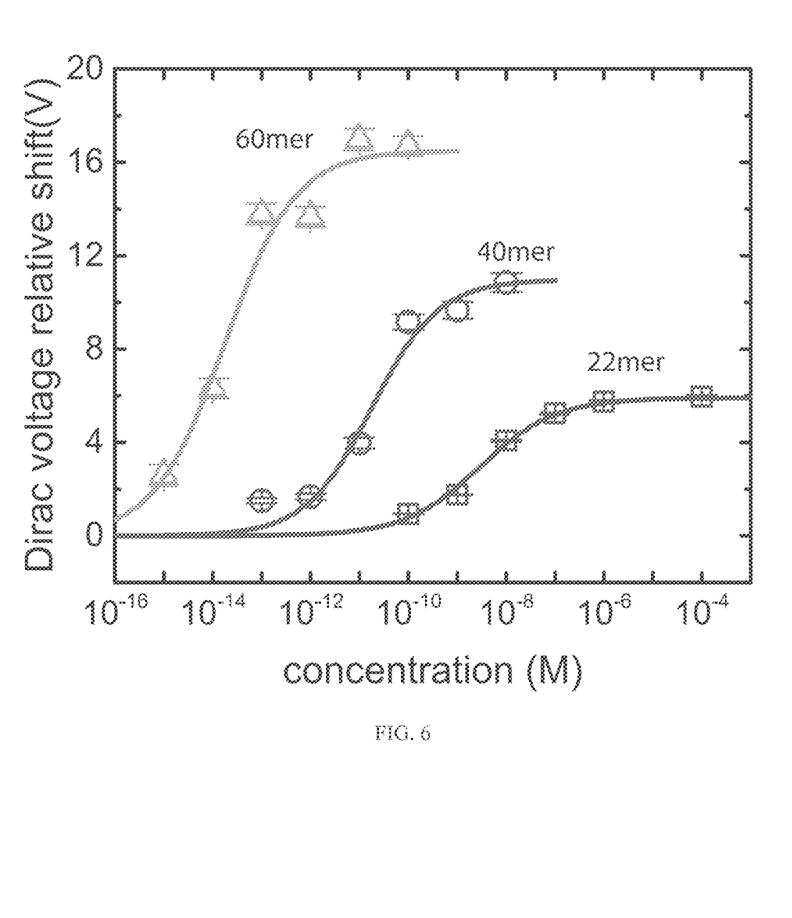
FIG. 6 provides relative Dirac voltage shift as a function of concentration for DNA targets of different lengths. Error bars (standard deviation of the mean) are approximately equal to the size of the plotted point. Solid curves are fits to the data based on the Sips model.

In addition to the DNA biosensors based on 22mer probe DNA, also tested were sensors based on 40mer probe DNA and 60mer probe DNA. The relative Dirac voltage shift was calculated by subtracting the buffer solution baseline, as shown in FIG. 6. The limit of detection (LOD) using 40mer probe DNA was ~100 fM, and the 60mer target DNA was reliably detected at an unexpected concentration of 1 fM (~6×10⁵ DNA molecules in a 1 mL drop).

Figure 7:
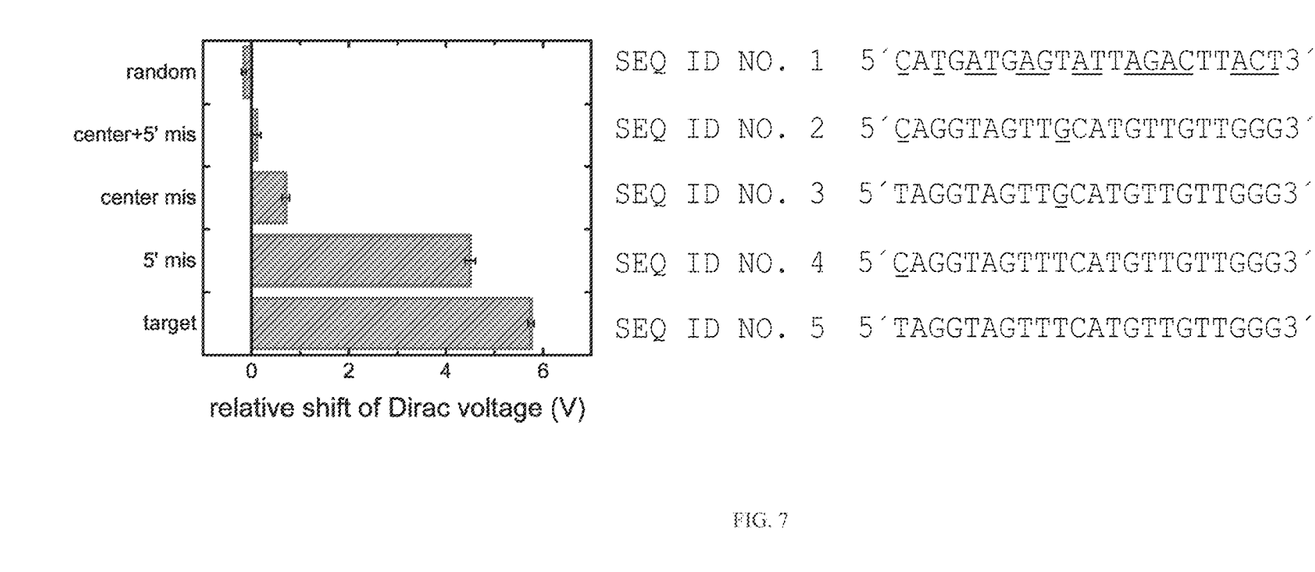
FIG. 7 provides the relative response of GFET-based 22mer DNA biosensors to the target sequence and various controls, all at a concentration of 1 µM. The base sequences of the oligomers tested are listed as SEQ ID NO: 1, SEQ ID NO: 2, SEQ ID NO: 3, SEQ ID NO: 4, SEQ ID NO: 5, with mismatches shown in red (underlined). Starting from the bottom, the oligomers tested are: target DNA, single mismatch at the 5' end, single mismatch at the center, two mismatches at the 5' end and the center, and random sequence DNA. Error bars are standard deviation of the mean.

Multiple control experiments (with concentration of 1 μM in DI water) were conducted with 22mer DNA biosensors to verify that the biosensor responses reflected specific binding of the complementary target DNA, as in FIG. 7.

The target 22mer DNA provided the largest value for the relative Dirac Voltage shift ($\Delta V_D^{REL}=5.7\pm0.4$ V), which is (without being bound to any particular theory) expected, as it should have the highest binding affinity for the probe DNA and therefore the largest response. The single base-mismatch controls are expected to interact more weakly with the probe DNA with affinity depending on the mismatch-position.

The control with a single base-mismatch at the 5' end showed a slight response decrease (~+4.6±0.7 V or 80±12% of that for the target DNA), while the response to control DNA with the mismatch at the center is strongly suppressed (+0.7±0.5 V), only ~10% of that for the target DNA.

Experiments based on DNA oligonucleotide microarrays show similar effects in how the response depends on the position of a single base mismatch. The control oligomer with two mismatches, one at the center and one at the 5' end, gave a sensor response that was indistinguishable from the response to DI water, and the same was true for the response to a 1 micromolar solution of a random sequence DNA oligomer (32% consistent with the target DNA).

Materials for Drug Biosensors

Also developed were biosensors for detecting drugs based on the technique for scalable transistor fabrication. The transistors were functionalized with ATW0067 (32mer, Base Pair Technologies), a DNA-based aptamer that binds specifically to a AIDS-treating/preventing drug target, Tenofovir (Sigma-Aldrich 1653601).

The graphene transistors were fabricated and functionalized with pyrene-NHS the same way as DNA biosensor fabrication. As the aptamer-functionalization step after the pyrene-NHS binds to graphene, the devices were incubated in a solution of aptamer in phosphate-buffer solution (PBS) with pH of 7.6. The solution was heated from 35 deg. C to 90 deg. C, held for 15 minutes, and cooled to room temperature in 25 minutes. The incubation period lasted for ~3 hours.

Figure 8:
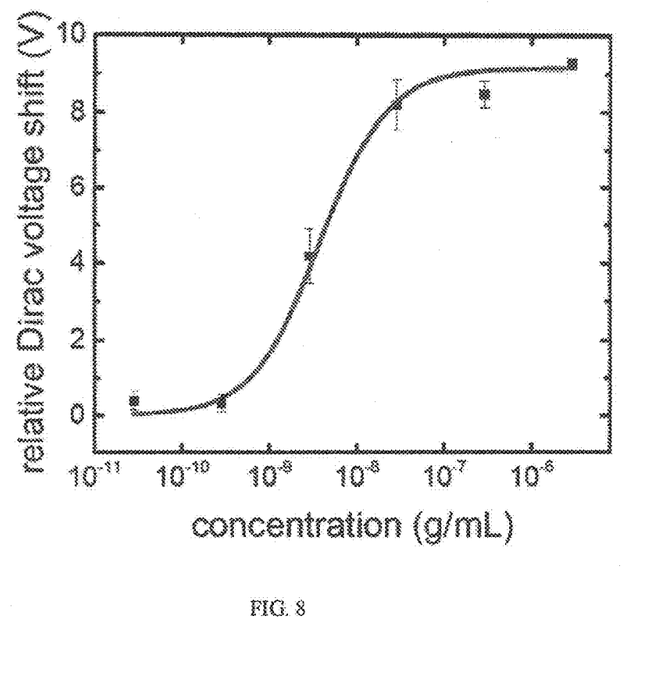
FIG. 8 provides the concentration of Tenofovir in 1 mL of DI water versus the relative shift in the Dirac voltage between aptamer attachment and drug attachment. All values are relative to the shift produced by DI water alone.

For testing Tenofovir concentration (FIG. 8), Tenofovir/DI water solutions of a known concentration were pipetted onto each GFET chip and left for one hour to allow the drug to bind to the aptamer.

To verify the selectivity of the aptamer's binding to the Tenofovir, three control drugs, Abacavir, Emtricitabine, and Lamivudine were tested, all at the same concentration of ~200 ng/mL. The response (relative shift of Dirac voltage) to the control drugs, $0.5\pm0.2$ V, $-0.1\pm0.1$, and $0.8\pm0.1$ V, respectively for Abacavir, Emtricitabine, and Lamivudine, is nearly negligible compare to the response to Tenofovir at the same concentration: $15.2\pm0.3$ V.

Comparison with Existing Technologies

The disclosed graphene-based DNA-decorated FETs are scalable, back-gated DNA biosensors of their kind, wherein multiple devices can be made at once. These devices feature an architecture that allows for multiple applications, including the monitoring of amplification products, the monitoring of ssDNA or other DNA, and the like. As one example, the disclosed technology may be useful in monitoring patients' adherence to a medication regimen.

ILLUSTRATIVE EMBODIMENTS

In one aspect, the present disclosure provides sensor devices. A sensor device may comprise a portion of graphene; and a polyaromatic molecule attached to and in electrical communication with the portion of graphene, the polyaromatic molecule comprising a leaving group configured to be displaced by an amine group or other nucleophile. "Polyaromatic molecule" includes so-called polycyclic aromatic hydrocarbons (PAHs), which may also be termed polyaromatic hydrocarbons.

A polyaromatic molecule may comprise at least two aromatic rings fused to one another. A polyaromatic molecule may also comprise from two to ten aromatic rings. Pyrene is considered a particularly suitable such polyaromatic molecule, although other polyaromatics are also suitable, e.g., anthracene, phenanthrene, tetracene, chrysene, triphenylene, pentacene, benzo[a]pyrene, corannulene, benzo[ghi]perylene, coronene, ovalene, and the like.

Polyaromatic molecules that support pi-pi orbital interactions between the polyaromatic molecule and graphene are considered especially suitable. The polyaromatic molecule may be attached to the portion of graphene via pi-pi orbital interaction, via covalent bonding, via ionic bonding, via hydrogen bonding, or any combination thereof. Attachment via pi-pi orbital interaction (e.g., pi-pi stacking) is considered especially suitable.

A polyaromatic molecule may include one or more leaving groups. Suitable such leaving groups include, e.g., isothiocyanate, isocyanate, acyl azide, NHS ester, sulfonyl chloride, aldehyde, glyoxal, epoxide, oxirane, carbonate, aryl halide, imidoester, carbodiimide, anhydride, fluorophenyl ester, or any combination thereof. Particularly suitable leaving groups may be, e.g., N-hydroxysuccinimide (NHS), sulfo-NHS, hydroxy benzotriazole (HOBt), 1-hydroxy-7-azabenzotriazole (HOAt), pentafluorophenol, or any combination thereof. N-hydroxysuccinimide (NHS) is considered especially suitable:other suitable leaving groups will be known to those of ordinary skill in the art.

The portion of graphene may be disposed on a substrate. A substrate may comprise silicon, silicon oxide, or any combination thereof. A substrate may be insulating, semiconducting, or even conducting. A device may be configured such that the substrate—or a portion of the substrate—is used as a backgate or other electrode of the device.

The portion of graphene may comprise single- or multi-layered graphene. The portion of graphene may be square, but may also be circular, polygonal, oblong, or otherwise shaped. The portion of graphene may, in some embodiments, have an aspect ratio of from 1:1 to 1:100,000, and all intermediate values, e.g., from 1:1 to 1:10,000, from 1:1 to 1:1,000, from 1:1 to 1:500, from 1:1 to 1:250, from 1:1 to 1:100, or even from 1:1 to 1:10.

The portion of graphene may be in electrical communication with at least one electrode. An electrode may comprise one or more metals, e.g., copper, gold, iron, chromium, and the like.

The present disclosure also provides further sensor devices. A sensor device may comprise a portion of graphene; and a polyaromatic molecule attached to and in electrical communication with the portion of graphene, the polyaromatic molecule being in electronic communication with a detection moiety configured to interact with a target molecule.

Suitable polyaromatic molecules are described elsewhere herein. A polyaromatic molecule may comprise at least two aromatic rings fused to one another. A polyaromatic molecule may also comprise from two to ten aromatic rings. Pyrene is considered an especially suitable polyaromatic molecule.

Also as described elsewhere herein, the polyaromatic molecule may be attached to the portion of graphene via pi-pi orbital interaction, via covalent bonding, via ionic bonding, via hydrogen bonding, or any combination thereof. Attachment via pi-pi orbital interactions is considered especially suitable.

A detection moiety may comprise a plurality of nucleotides. A detection moiety may be, e.g., an oligonucleotide, an aptamer, or any combination thereof. A detection moiety may also comprise a plurality of amino acids, e.g., a protein. A ssDNA aptamer is a suitable detection moiety.

The present disclosure also provides methods. These methods may comprise contacting a sensor device according to the present disclosure with a sample; and measuring an electrical signal of the device related to an interaction between the detection moiety and the sample.

Suitable electrical signals include, e.g., currents, voltages (e.g., a Dirac voltage), resistances, and the like. Current signals are considered especially suitable.

A sample may comprise a target molecule. A target molecule may be present at, e.g., less than 200 pM. A sample may be a biological material obtained from a subject. A sample may also be a biological material that has been processed, e.g., centrifuged, reacted, or otherwise processed.

Target molecules may be, e.g., proteins, polynucleotides, and the like. Polynucleotides (e.g., ssDNA or other DNA) are considered especially suitable targets.

It should be understood that the methods may also include contacting the device to a plurality of samples. This may be accomplished by, e.g., contacting different graphene portions of a device with different samples and monitoring a signal from each of the different graphene portions. In this way, a user may simultaneously analyze a plurality of samples.

Further disclosed are methods, the methods comprising contacting a sample to a detection moiety attached to a portion of graphene, the detection moiety being attached to a polyaromatic molecule in electrical communication with a portion of graphene; and measuring an electrical signal of the device related to an interaction between the detection moiety and the sample.

Suitable polyaromatic molecules, graphene, samples, signals, and detection moieties are described elsewhere herein.

Also provided are methods of fabricating detector devices, comprising: attaching a polyaromatic molecule to a portion of graphene so as to place the polyaromatic molecule into electrical communication with the portion of graphene: attaching a detection moiety to the polyaromatic molecule; and placing the portion of graphene into electrical communication with at least one electrode.

The disclosed methods may also comprise disposing the portion of graphene on a substrate. Suitable substrates are described elsewhere herein.

Attaching a polyaromatic molecule may be effected by pi-pi orbital interaction, by covalent bonding, by ionic bonding, by hydrogen bonding, or any combination thereof.

Attaching a detection moiety to the polyaromatic molecule may be effected by a displacement reaction. A displacement reaction may comprise a substitution reaction in which the detection moiety displaces a leaving group from the polyaromatic molecule.

The methods may include disposing the graphene, one or more electrodes, or any of the foregoing on a substrate. Suitable substrates include silicon and silicon oxide:other substrate materials are also suitable and will be known to the user of ordinary skill in the art. Electrodes may be formed on the substrate, and gaps/channels may then be formed between the electrodes.

A device may be fabricated such that the device comprises one, two, three, or more portions of graphene that are individually electrically addressable. In this way, a user may form multiplexed or array-type devices that allow for simultaneous analysis of multiple samples at one time.

It should be understood that disclosed technology may also applied to non-DNA molecular targets.

Also provided are method, comprising contacting, with a molecule that comprises an amine, a device that comprises a portion of graphene, a polyaromatic molecule attached to and in electrical communication with the portion of graphene, the polyaromatic molecule comprising a leaving group configured to be displaced by an amine group, under such conditions that the amine displaces the leaving group so as to effect a covalent bond between the molecule and the polyaromatic molecule.

The molecule may comprise a detection moiety; suitable such detection moieties are described elsewhere herein. A detection moiety may comprise a plurality of nucleotides, a plurality of amino acids, or any combination thereof.

What is claimed:

1. A sensor comprising: an array of graphene devices, said array comprising a plurality of sensor devices, each said device comprising:
   a portion of graphene;
   a polyaromatic molecule attached to and in electrical communication with the portion of graphene,
   the polyaromatic molecule comprising a leaving group configured to be displaced by an amine group,
   at least one of the graphene devices comprising a channel having dimensions of about 10 microns by about 100 microns.

2. A sensor device, comprising:
   a portion of graphene in communication with at least one electrode;
   a polyaromatic molecule attached to and in electrical communication with the portion of graphene; and
   a detection moiety attached via a linkage to said polyaromatic molecule, said detection moiety comprising a ssDNA.

3. The sensor device of claim 2, wherein said linkage comprises the product of a nucleophilic attack of said ssDNA upon said polyaromatic molecule.

4. The sensor device of claim 3, wherein said polyaromatic molecule is selected from the group consisting of: anthracene, phenanthrene, tetracene, chrysene, triphenylene, pentacene, benzo[a] pyrene, corannulene, benzo[ghi] perylene, coronene, ovalene, and pyrene.

5. The sensor device of claim 3, wherein said polyaromatic molecule comprises two to ten aromatic rings.

6. The sensor device of claim 3, wherein said polyaromatic molecule is attached to the portion of graphene via pi-pi orbital interaction.

7. The sensor device of claim 3, wherein said polyaromatic molecule is attached to the portion of graphene via covalent bonding, via ionic bonding, or via hydrogen bonding.

8. The sensor device of claim 5, wherein said polyaromatic molecule is attached to the portion of graphene via pi-pi orbital interaction.

9. A method of fabricating a detector device, comprising: attaching a polyaromatic molecule selected from the group consisting of: anthracene, phenanthrene, tetracene, chrysene, triphenylene, pentacene, benzo[a] pyrene, corannulene, benzo[ghi] perylene, coronene, or ovalene to a portion of graphene so as to place the polyaromatic molecule into electrical communication with the portion of graphene; and
   attaching a ssDNA detection moiety to the polyaromatic molecule.

10. The method of claim 9, wherein said attaching the ssDNA detection moiety to the polyaromatic molecule comprises ssDNA nucleophilic attack upon said polyaromatic molecule.

11. The method of claim 9, wherein attaching the molecule of anthracene, phenanthrene, tetracene, chrysene, triphenylene, pentacene, benzo[a] pyrene, corannulene, benzo[ghi] perylene, coronene, or ovalene is effected by pi-pi orbital interaction, by covalent bonding, by ionic bonding, by hydrogen bonding, or any combination thereof.

12. A method to detect the presence of a DNA sequence, comprising: contacting a sample comprising said DNA sequence to a device according to claim 2,
   said device featuring a current-gate voltage characteristic with a Dirac voltage;
   monitoring the Dirac voltage on the current-gate voltage characteristic; and
   obtaining a concentration-dependent shift in the Dirac voltage.

* * * * *

UNITED STATES PATENT AND TRADEMARK OFFICE
CERTIFICATE OF CORRECTION

PATENT NO. : 12,379,343 B2
APPLICATION NO. : 17/934540
DATED : August 5, 2025
INVENTOR(S) : Alan T. Johnson, Jr. et al.

It is certified that error appears in the above-identified patent and that said Letters Patent is hereby corrected as shown below:

In the Specification

Under Column no. 1, Line no. 13, Replace:
"2018):"
With:
--2018);--

Under Column no. 2, Line no. 10, Replace:
"FETs:"
With:
--FETs;--

Under Column no. 2, Line no. 35, Replace:
"graphene:"
With:
--graphene;--

Under Column no. 2, Line no. 55, Replace:
"graphene:"
With:
--graphene;--

Under Column no. 3, Line no. 12, Replace:
"follows:"
With:
--follows;--

Signed and Sealed this
Thirtieth Day of September, 2025

John A. Squires
*Director of the United States Patent and Trademark Office*

Under Column no. 3, Line no. 13, Replace:
"probe:"
With:
--probe;--

Under Column no. 3, Line no. 16, Replace:
"blue:lower"
With:
--blue; lower--

Under Column no. 3, Line no. 17, Replace:
"(blue:middle"
With:
--(blue; middle--

Under Column no. 3, Line no. 18, Replace:
"blue:top"
With:
--blue; top--

Under Column no. 3, Line no. 19, Replace:
"traces):"
With:
--traces);--

Under Column no. 3, Line no. 22, Replace:
"attachment:"
With:
--attachment;--

Under Column no. 3, Line no. 25, Replace:
"V):"
With:
--V);--

Under Column no. 3, Line no. 31, Replace:
"equation:"
With:
--equation;--

Under Column no. 3, Line no. 36, Replace:
"model:"
With:
--model;--

CERTIFICATE OF CORRECTION (continued)

Under Column no. 3, Line no. 66, Replace:
""a.""
With:
--"a,"--

Under Column no. 4, Line no. 65, Replace:
"µM"
With:
--uM--

Under Column no. 5, Line no. 12, Replace:
"below:"
With:
--below--

Under Column no. 6, Line no. 23, Replace:
"500)"
With:
--500--

Under Column no. 6, Line no. 30, Replace:
"luM"
With:
--1 uM--

Under Column no. 8, Line no. 8, Replace:
"hydroxy benzotriazole"
With:
--hydroxybenzotriazole--

Under Column no. 8, Line no. 11, Replace:
"suitable:other"
With:
--suitable; other--

Under Column no. 9, Line no. 23, Replace:
"graphene:"
With:
--graphene;--

Under Column no. 10, Line no. 8, Replace:
"oxide:other"
With:
--oxide; other--

CERTIFICATE OF CORRECTION (continued)
U.S. Pat. No. 12,379,343 B2

In the Claims

Under Column no. 11, Claim 4, Line no. 33, Replace:
"benzo[a] pyrene,"
With:
--benzo[a]pyrene,--

Under Column no. 11, Claim 4, Line nos. 33-34, Replace:
"benzo[ghi] perylene,"
With:
--benzo[ghi]perylene,--

Under Column no. 12, Claim 9, Line no. 14, Replace:
"benzo[a] pyrene,"
With:
--benzo[a]pyrene,--

Under Column no. 12, Claim 9, Line no. 15, Replace:
"benzo[ghi] perylene,"
With:
--benzo[ghi]perylene,--

Under Column no. 12, Claim 11, Line no. 28, Replace:
"benzo[a] pyrene,"
With:
--benzo[a]pyrene,--

Under Column no. 12, Claim 11, Line nos. 28-29, Replace:
"benzo[ghi] perylene,"
With:
--benzo[ghi]perylene,--